US00PP21002P2

(12) United States Plant Patent
Fitzgerald

(10) Patent No.: US PP21,002 P2
(45) Date of Patent: May 18, 2010

(54) ***CAREX* PLANT NAMED 'EVERILLO'**
(50) Latin Name: *Carex oshimensis*
Varietal Denomination: Everillo

(76) Inventor: Pat Fitzgerald, Old Town, Stoneyford, Co. Kilkenny (IE)

( * ) Notice: Subject to any disclaimer, the term of this patent is extended or adjusted under 35 U.S.C. 154(b) by 0 days.

(21) Appl. No.: 12/383,526

(22) Filed: Mar. 25, 2009

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent L Bell
(74) *Attorney, Agent, or Firm*—Penny J. Aguirre

(57) ABSTRACT

A new cultivar of *Carex oshimensis*, 'Everillo', characterized its foliage that is uniformly yellow in color, its compact clump-forming growth habit, its ability to be readily propagated by rhizome division and basal cuttings, and its hardiness at least in U.S.D.A. Zones 6 to 9.

2 Drawing Sheets

Botanical classification: *Carex oshimensis.*
Varietal denomination: 'Everillo'.

BACKGROUND OF THE INVENTION

The present invention relates to a new and distinct cultivar of *Carex oshimensis* and will be referred to hereafter by its cultivar name, 'Everillo'. 'Everillo' is a new cultivar of perennial ornamental grass grown for container and landscape use, primarily in shaded exposures.

The new cultivar, 'Everillo' arose as a naturally occurring whole plant chimeral mutation of *Carex oshimensis* 'Evergold' (not patented). The Inventor discovered 'Everillo' in August of 2007 in a container at his nursery in Oldtown, Stoneyford, Co. Kilkenny, Republic of Ireland.

Asexual reproduction of the new cultivar was first accomplished by rhizome division in Oldtown, Stoneyford, Co. Kilkenny, Republic of Ireland in January of 2008 by the Inventor. The characteristics of this cultivar have been determined to be stable and are reproduced true to type in successive generations.

SUMMARY OF THE INVENTION

The following traits have been repeatedly observed and represent the characteristics of the new cultivar. The new *Carex* has not been observed under all possible environmental conditions. These attributes in combination distinguish 'Everillo' from all other selections of *Carex* known to the Inventor.

1. 'Everillo' exhibits foliage that is uniformly yellow in color.
2. 'Everillo' exhibits a plant habit that slowly spreads by rhizomes and forms compact clumps as it matures.
3. 'Everillo' is readily propagated by rhizome division and basal cuttings.
4. 'Everillo' is hardy at least in U.S.D.A. Zones 6 to 9.

'Everillo' has a similar plant habit and growth rate to its parent plant, 'Evergold', however 'Everillo' exhibits leaves that are solid yellow in color, whereas the leaves of 'Evergold' are variegated with creamy-yellow centers and green margins. There are no other cultivars of *Carex oshimensis* known to the Inventor that exhibit foliage that is solid yellow in color. 'Everillo' can be most closely compared to cultivars of *Carex*

*elata*; 'Bowles Golden' (syn. 'Aurea'), which has yellow foliage with a very narrow green edge and 'Knight Shayes', which is a solid yellow-leaved mutation of 'Bowles Golden' (both unpatented). These cultivars are not only a different species but develop into larger sized plants in comparison to 'Everillo' with a mature size of about 70 cm in height and 45 cm in width.

BRIEF DESCRIPTION OF THE DRAWING

The accompanying colored photographs illustrate the overall appearance and distinct characteristics of six month-old plants of the new *Carex* as grown in 9-cm containers outdoors in Oldtown, Stoneyford, C. Kilkenny, Ireland.

The photograph in FIG. 1 illustrates the overall plant habit and appearance of 'Everillo'.

Figure 1:
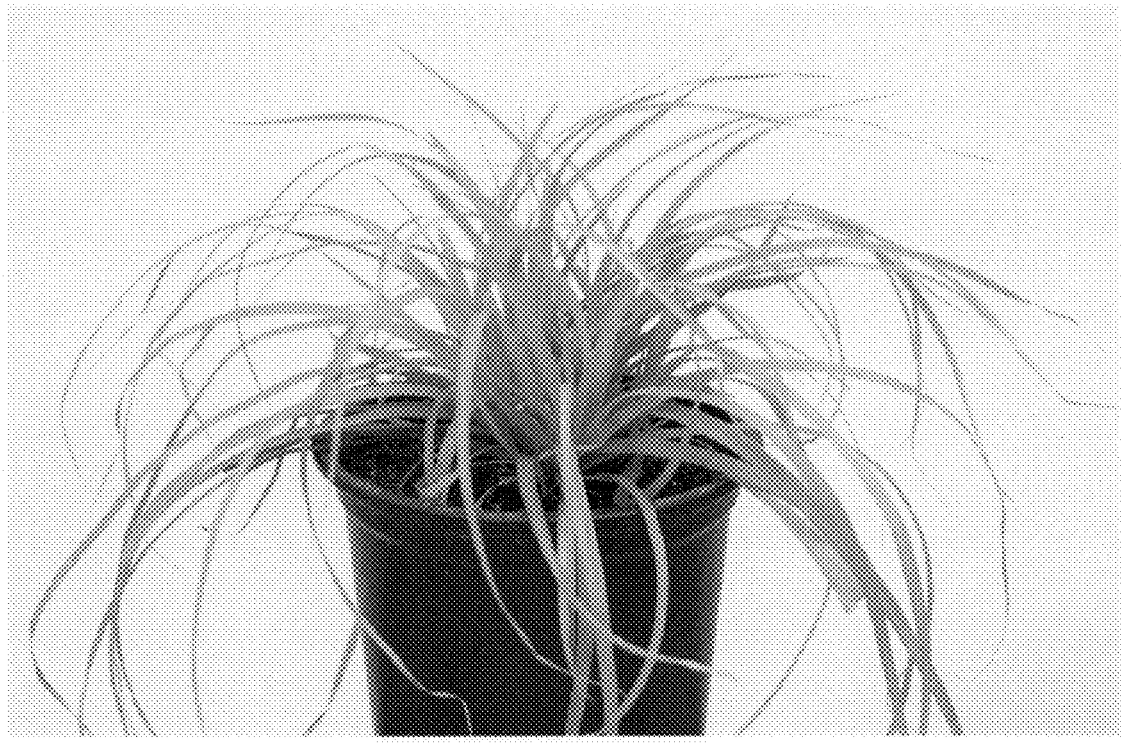
Figure 2:
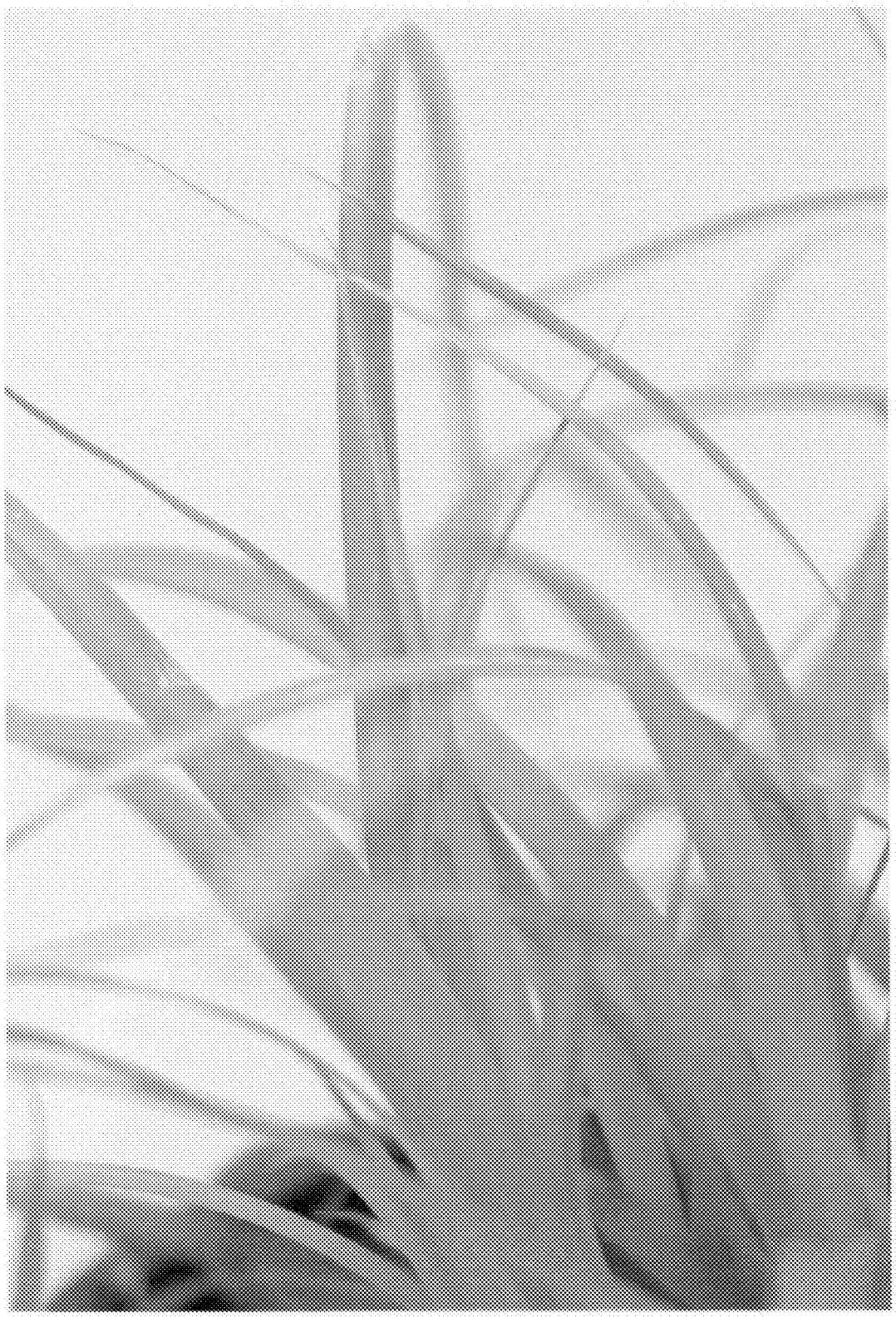

The photograph in FIG. 2 provides a detailed close-up view of the leaf-shape and yellow leaf coloration.

The colors in the photograph may differ slightly from the color values cited in the detailed botanical description, which accurately describe the colors of the new *Carex*.

DETAILED BOTANICAL DESCRIPTION

The general observations and descriptions describe plants of 'Everillo' as grown outdoors in a nursery in 9-cm containers in Co. Kilkenny, Republic of Ireland for six months from a single rhizome division. The phenotype may vary somewhat with variations in temperature, day-length, light intensity, soil types, and water and fertility levels without, however, any variance in genotype. The color determinations are in accordance with the 2001 R.H.S Colour Chart of The Royal Horticultural Society, London, England, except where general color terms of ordinary dictionary significance are used.

General description:

*Blooming period.*—Inflorescences emerge in January and continue into summer in the Republic of Ireland.

*Plant habit.*—Herbaceous clump-forming ornamental perennial grass, evergreen at least to U.S.D.A. Zone 6, flattened-globular mound in shape.

*Growth habit.*—Broad, spreading.

*Height and spread.*—Reaches about 8.4 cm in height, spreads to about 19.4 cm in diameter.

*Hardiness.*—At least in U.S.D.A. Zones 6 to 9.

*Culture.*—Grows best in part shade in fertile, well-drained soils with adequate moisture, tolerant to full shade in warmer climates and full sun in cooler climates.

*Diseases and pests.*—No increased susceptibility or resistance to diseases or pests has been observed.

*Root description.*—Short, stout rhizomes with dense, fibrous roots, roots moderately branched.

Growth and propagation:

*Propagation.*—Rhizome division and basal cuttings.

*Root initiation from cuttings.*—About 4 weeks at 20° C. and produce fully rooted liner in about 3 months.

*Root development from division.*—Fully develop in 9-cm containers in about 9 months from rhizome divisions.

*Growth rate.*—Moderate.

*Branching.*—Stemless, shoots arise from rhizomes, about 18 divisions develop per clump in a 6 month production schedule.

Foliage description:

*Leaf shape.*—Linear, curved.

*Leaf division.*—Simple.

*Leaf base.*—Sheathed to rhizome, triangular in shape.

*Leaf apex.*—Attenuate.

*Leaf aspect.*—Leaves initially emerge upright, then cascade outward and finally arch downward until the terminal blades lay on the ground.

*Leaf venation.*—Parallel, the midrib is raised on the lower surface, not prominent or conspicuous, color matches leaf color.

*Leaf margins.*—Entire, slightly scaberulose.

*Leaf persistence.*—Persistent; evergreen under conditions tested.

*Leaf size.*—Matures to an average of 16.4 cm in length and 5 mm in width.

*Leaf number.*—Average of 5 leaves per rhizome and about 90 per plant.

*Leaf arrangement.*—Equitant (overlapping), emerge from center, sheathed to base.

*Leaf surface.*—Moderately glossy, glabrous, smooth.

*Leaf durability to stress.*—High.

*Leaf color.*—Young emerging leaves and mature leaves upper surface; 145A, base slightly lighter 149A, lower surface young leaves 145A matures to 144B to 144C.

Flower description:

*General description.*—Terminal racemes of gynaecandrous spikelets.

*Inflorescence size.*—Averages 2.4 cm in height and 4 mm in width.

*Flower quantity per inflorescence.*—Typically one floret per spikelet; about 20% are staminate and 80% are pistillate, an average 100 spikelets per raceme.

*Lastingness of inflorescence.*—Flowers last about 10 days.

*Flowering season.*—Continuous from January into summer in Ireland.

*Response time to flower.*—Approximately 8 months.

*Rate of flower opening.*—After first initial flowers open in an inflorescence all flowers open within 3 weeks.

*Fragrance.*—None.

*Floret buds.*—Narrowly ovate in shape, about 2 mm in length and about 1 mm in diameter, 145 D in color.

*Spikelet aspect.*—Upright.

*Spikelet shape.*—Sedge-like, narrowly ovate.

*Persistence of spikelets.*—Persistant.

*Floret (spikelet) size.*—Staminate florets; an average of 4 mm in diameter and 1 cm in length, pistillate florets; an average of 1.5 mm in diameter and 1 cm in length.

*Floret (spikelet) description.*—1 glume on outer side and 1 lemma on inner side on staminate florets and 1 lemma on inner side of pistillate florets (lack glumes), glumes; an average of 8 mm in length and 0.5 mm in width, lanceolate in shape, margin entire, apex narrowly acute, color of upper and lower surface 165C, surface is smooth and dull in appearance, lemma; an average of 8 mm in length and 1 mm in width, lanceolate in shape, margin entire, apex long and mucronate, color of upper and lower surface on staminate florets 165C, color of upper and lower surface on pistillate florets 164C to 164D with central vein 143B to 143C, surface is smooth and dull in appearance.

*Rachis.*—An average of 1.5 cm in length and 1 mm in diameter, held upright, strong, 144B to 145A in color.

Reproductive organs:

*Gynoecium.*—Average of 3 pistils about 1 mm in length, stigma is fimbriate and 199B to 199C in color, style is about 0.2 mm in length, insufficient in size to be color coded, ovary is 157A to 192D in color.

*Androcoecium.*—Average of 3 stamens, basifixed, about 2 mm in length and 164C to 164D in color, pollen production very low and insufficient in quantity to be color coded.

*Fruits and seeds.*—Seed production has not been observed to date.

It is claimed:

1. A new and distinct cultivar of *Carex* plant named 'Everillo' as herein illustrated and described.

* * * * *